US007497216B2

(12) United States Patent
Forsyth et al.

(10) Patent No.: US 7,497,216 B2
(45) Date of Patent: Mar. 3, 2009

(54) SELF CONTAINED BREATHING APPARATUS MODULAR CONTROL SYSTEM

(76) Inventors: David E. Forsyth, 1274 Glenneyre St., Laguna Beach, CA (US) 92651; Wayne K. Miller, 12001 Quartz Valley Rd., Fort Jones, CA (US) 96032

( * ) Notice: Subject to any disclaimer, the term of this patent is extended or adjusted under 35 U.S.C. 154(b) by 449 days.

(21) Appl. No.: 11/215,363

(22) Filed: Aug. 30, 2005

(65) Prior Publication Data

US 2006/0201509 A1 Sep. 14, 2006

Related U.S. Application Data

(60) Provisional application No. 60/605,561, filed on Aug. 30, 2004.

(51) Int. Cl.
*A61M 16/00* (2006.01)

(52) U.S. Cl. ........................... 128/204.21; 128/204.22; 128/204.29; 128/201.27

(58) Field of Classification Search ............ 128/204.21, 128/201.27, 205.28, 204.26, 204.29, 205.11, 128/914, 204.22
See application file for complete search history.

(56) References Cited

U.S. PATENT DOCUMENTS

| | | | | |
|---|---|---|---|---|
| 2,830,583 | A | 4/1958 | Finney | |
| 3,111,946 | A | 11/1963 | Galeazzi | |
| 3,215,057 | A | 11/1965 | Turek | |
| 3,252,458 | A | 5/1966 | Krasberg | |
| 3,556,098 | A | 1/1971 | Kanwisher et al. | |
| 3,587,438 | A | 6/1971 | Foster et al. | |
| 3,593,735 | A | 7/1971 | Reiher | |
| 3,656,196 | A | 4/1972 | Oniell et al. | |
| 3,672,388 | A | 6/1972 | Ringwall et al. | |
| 3,692,026 | A | 9/1972 | Tepper et al. | |
| 3,727,626 | A | 4/1973 | Kanwisher et al. | |
| 3,794,059 | A | 2/1974 | Burt, Jr. | |
| 3,934,581 | A | 1/1976 | O'Niell | |
| 3,957,043 | A | 5/1976 | Shelby | |
| 4,056,098 | A | 11/1977 | Michel et al. | |
| 4,236,546 | A | 12/1980 | Manley et al. | |
| 4,299,216 | A | 11/1981 | Bernard | |
| 4,313,743 | A | 2/1982 | Wallace | |
| 4,327,437 | A | 4/1982 | Frosch et al. | |
| 4,336,590 | A * | 6/1982 | Jacq et al. | 128/204.21 |
| 4,350,662 | A | 9/1982 | Dowgul et al. | |
| 4,440,162 | A | 4/1984 | Sewell et al. | |
| 4,554,942 | A | 11/1985 | Williams et al. | |
| 4,672,997 | A | 6/1987 | Landis et al. | |
| 4,738,693 | A | 4/1988 | Tom | |
| 4,939,647 | A | 7/1990 | Clough et al. | |
| 4,964,404 | A | 10/1990 | Stone | |
| 4,970,897 | A * | 11/1990 | Budinger | 73/432.1 |
| 4,989,160 | A | 1/1991 | Garrett et al. | |
| 5,048,565 | A | 9/1991 | Oi | |
| 5,440,477 | A | 8/1995 | Rohrberg et al. | |
| 5,503,145 | A | 4/1996 | Clough | |
| 5,566,713 | A | 10/1996 | Lhomer et al. | |

(Continued)

*Primary Examiner*—Steven O Douglas
(74) *Attorney, Agent, or Firm*—Dorsey & Whitney LLP

(57) ABSTRACT

The claim over prior art is for an approach to an electronically controlled or electronically monitored breathing system that represents an improvement in electrical reliability, manufacturing cost and efficiency, user maintenance, system reliability, user cost and maintenance. These improvements are accomplished by placing the major electronic, mechanical and electromechanical control elements and sensor components in a single replaceable module.

17 Claims, 6 Drawing Sheets

U.S. PATENT DOCUMENTS

| | | | | | |
|---|---|---|---|---|---|
| 5,570,688 | A | * | 11/1996 | Cochran et al. | 128/205.23 |
| 5,605,179 | A | | 2/1997 | Strong, Jr. et al. | |
| 5,662,143 | A | | 9/1997 | Caughran | |
| 5,794,645 | A | | 8/1998 | Rohrberg et al. | |
| 5,806,514 | A | * | 9/1998 | Mock et al. | 128/204.23 |
| 5,832,916 | A | | 11/1998 | Lundberg | |
| 6,003,513 | A | | 12/1999 | Readey et al. | |
| 6,186,177 | B1 | | 2/2001 | Maher | |
| 6,302,106 | B1 | * | 10/2001 | Lewis | 128/204.22 |
| 6,648,021 | B2 | | 11/2003 | Zheng et al. | |
| 6,712,071 | B1 | | 3/2004 | Parker | |
| 6,817,359 | B2 | | 11/2004 | Deas et al. | |
| 7,353,824 | B1 | * | 4/2008 | Forsyth et al. | 128/204.22 |

* cited by examiner

SELF CONTAINED BREATHING APPARATUS MODULAR CONTROL SYSTEM

CROSS REFERENCE TO RELATED APPLICATION(S)

The present utility patent application claims benefit of U.S. Provisional Application Ser. No. 60/605,561, filed Aug. 30, 2004 in the names of the present applicants, subject matter of which is incorporate herewith by reference.

FIELD OF THE INVENTION

The present invention relates: generally to respiratory methods or devices supplying respiratory gas under positive or ambient pressure; more specifically to electric control means for the supply of respiratory gas under positive or ambient pressure; most particularly to electric control means for the supply of respiratory gas under positive or ambient pressure by a respiratory method or device utilizing means for sensing partial pressure of a gas constituent.

BACKGROUND OF THE INVENTION

Breathing devices like Closed and Semi Closed Circuit Rebreathers and other closed loop breathing systems rely on electronic control systems to monitor the oxygen level through the use of oxygen sensors and to process the system information to determine if a solenoid or valve needs to be opened in order to add more oxygen into the breathing system. Up to now, this has involved a complicated and interconnected array of components to accomplish this task. The batteries, control electronics, sensors, and gas control devices all must be connected with cables and varying levels of connectors. Breathing systems to date have neither considered these subcomponents as a complete system nor have the control systems in general been considered as an integral part of the system design for the rebreather itself. The resultant breathing system designs have therefore treated the control system as both a separate system from the rebreather and have considered the individual components of the electronic control and sensing system as generally separate design elements. All of the control system subcomponents and parts have maintenance and reliability issues that either requires regular maintenance or possible replacement. All of the necessary electronic and mechanical interconnects between these components represent points of failure as well as increases assembly time, maintenance, and system cost.

All breathing device control systems require maintenance and have attendant diagnosis and or possible replacement issues. Successful diagnosis and replacement can be as easy as replacing a battery or sensor to as complicated as sending the entire breathing unit in for a factory trained technician to diagnose and service. The latter option comes at an additional cost of significant down time. On current, non-modular systems, parts can be very difficult to remove and replace; especially in the field or on short notice. A significant array of available spare parts is therefore necessary to be able to repair any control related failure in most breathing systems.

Manufacturer upgrades to the control system typically consists of sending the entire unit or a significant portion thereof back for retrofitting. This is both costly and inefficient.

In rebreathing systems, a popular implementation has been that the separate pieces have been combined into a single large "head" which comprises the entire top assembly of a rebreather. This "head" typically including breathing hose mounts, scrubber and breathing bag supply paths, some of the electronics, sensors and or the gas injection solenoid. The "head" therefore, is a substantially sized and priced piece of the breathing system with a great deal more functionality and cost than just the control subsystem and includes a great deal of mechanically oriented parts and mountings which are not as likely to fail or need replacement as the control and sensing subsystem. Within the "head", the components of the control and sensing subsystem are still treated as individual components with all the attendant difficulties remaining concerning cost and reliability.

SUMMARY OF THE INVENTION

The invention is summarized by considering that manufacturers and users of breathing systems are concerned with costs, reliability maintenance, and serviceability of these breathing systems. Claims are made for Closed and Semi Closed configurations of rebreathing systems that minimize electronic and mechanical failures by incorporating the microcontroller and associated electronics, measurement subsystem electronics, input and output cabling, connectors, gas control solenoids and software into a single removable module. Claims are made for the integration of the low pressure Oxygen, intra-stage Oxygen pressure, high pressure gas supply and ambient barometric pressure measurement subsystems and for the integration of the controller power supply. Claims are also made for wireless transmission of the data to and from the sensors and or measurement subsystems and to and from the user interface via the display subsystems. A claim is also made for the integration of a Personal Alert Safety Subsystem into the modular controller. This single module approach offers significant benefits in manufacturability, reliability, serviceability and maintenance. The additional benefit of reducing the technical knowledge required to perform maintenance and replacement tasks is also realized.

BRIEF DESCRIPTION OF THE DRAWINGS

The accompanying drawings which are incorporated in and form a part of the specification illustrate preferred embodiments of the present invention and, together with a description, serve to explain the principles of the invention. In the drawings.

DETAILED DESCRIPTION OF PREFERRED EMBODIMENT

Figure 1:
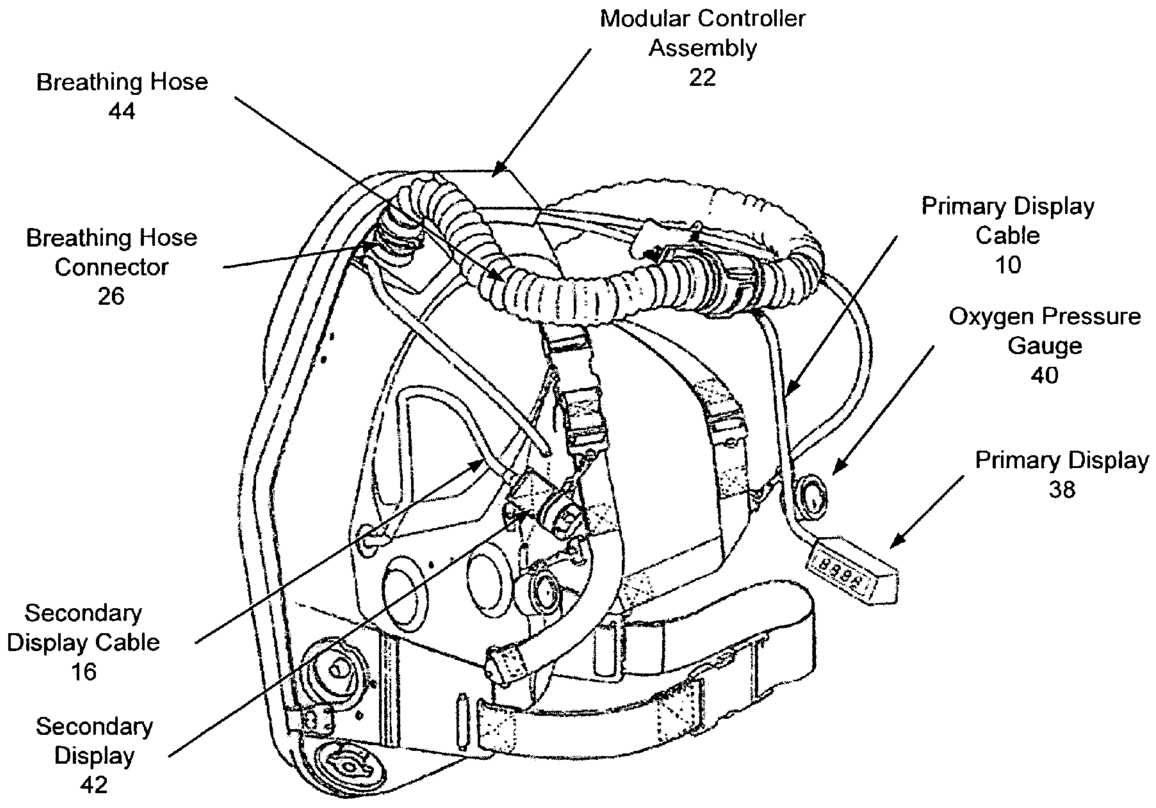
FIG. 1 is a picture of a complete electronically controlled mixed gas closed circuit rebreather.
Figure 2:
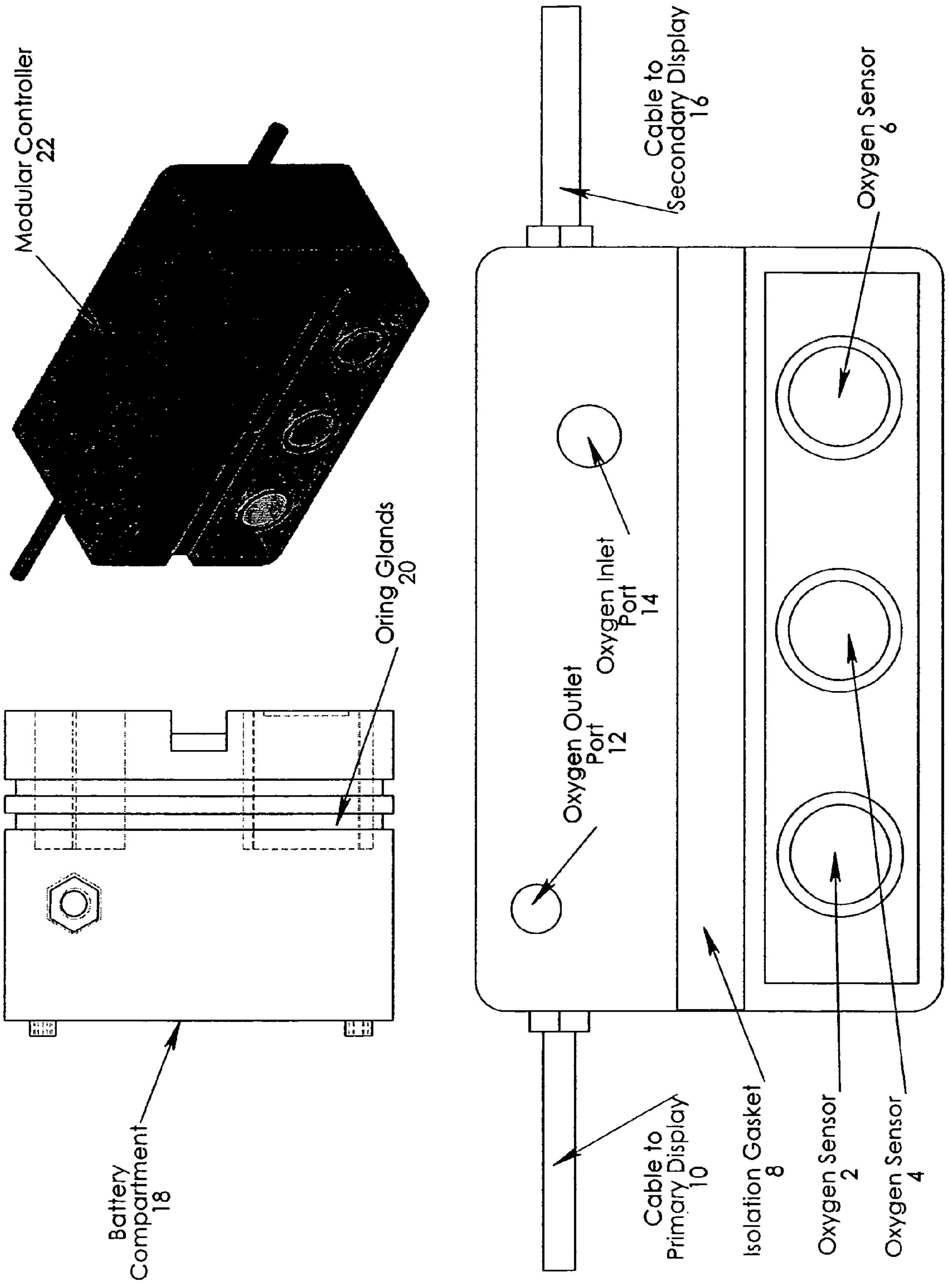
FIG. 2 is a drawing of one example of a modular controller assembly.
Figure 3:
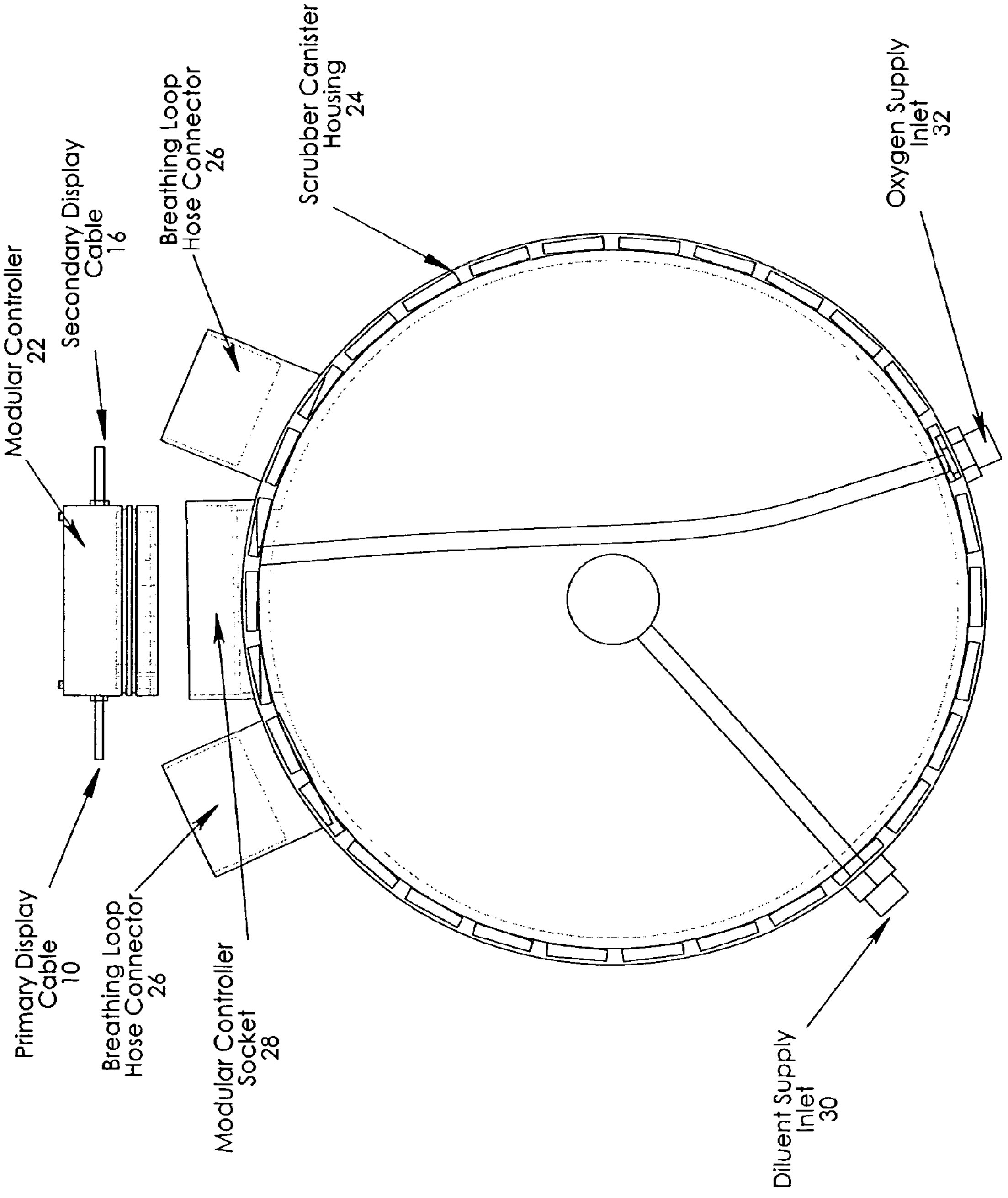
FIG. 3 is a front view drawing of one example of the interface between the modular controller and scrubber assembly.
Figure 4:
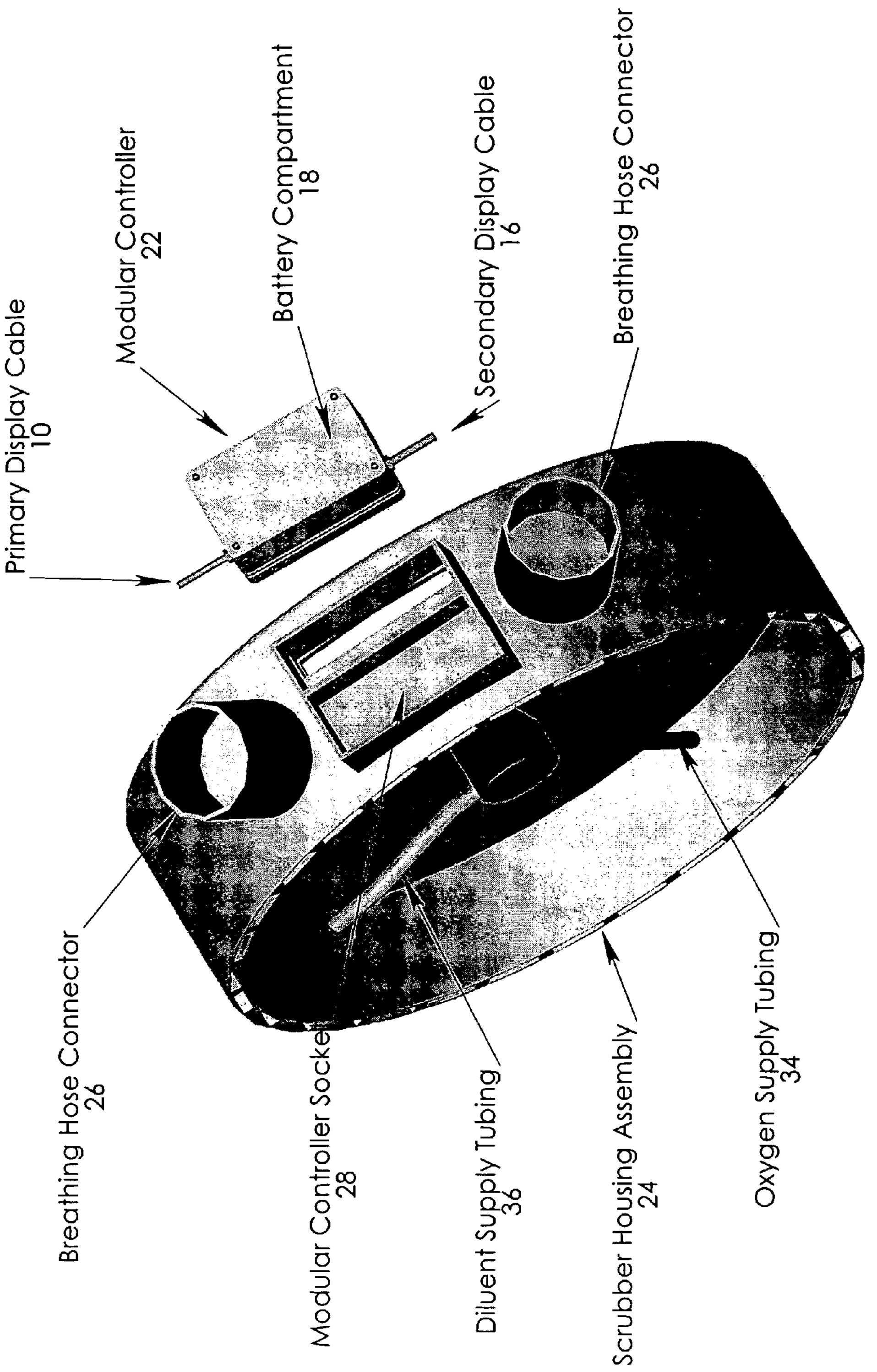
FIG. 4 is a ¾ view drawing of one example of the interface between the modular controller and scrubber assembly.
Figure 5:
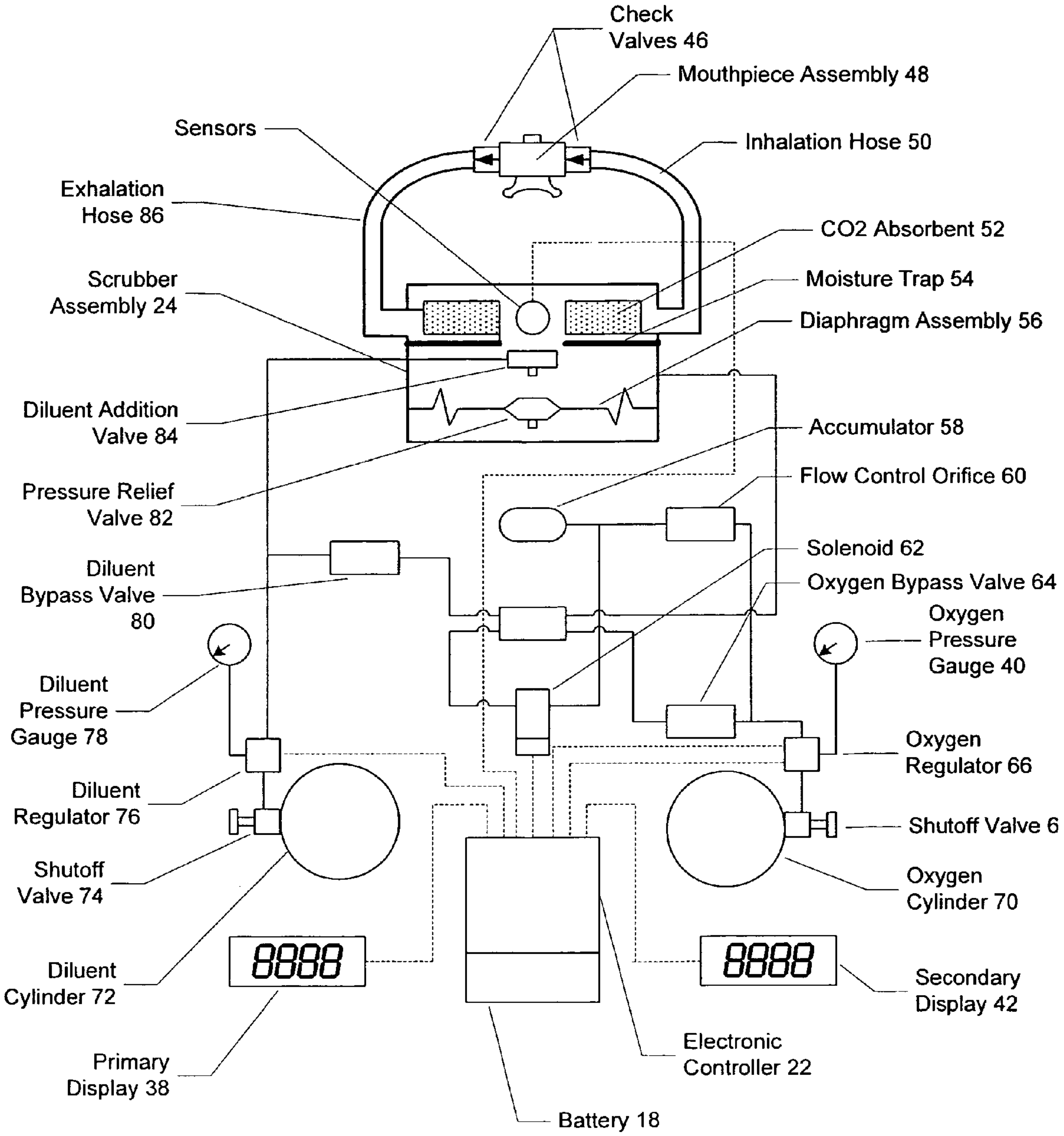
FIG. 5 is a schematic representation of a mixed gas closed circuit rebreather.
Figure 6:
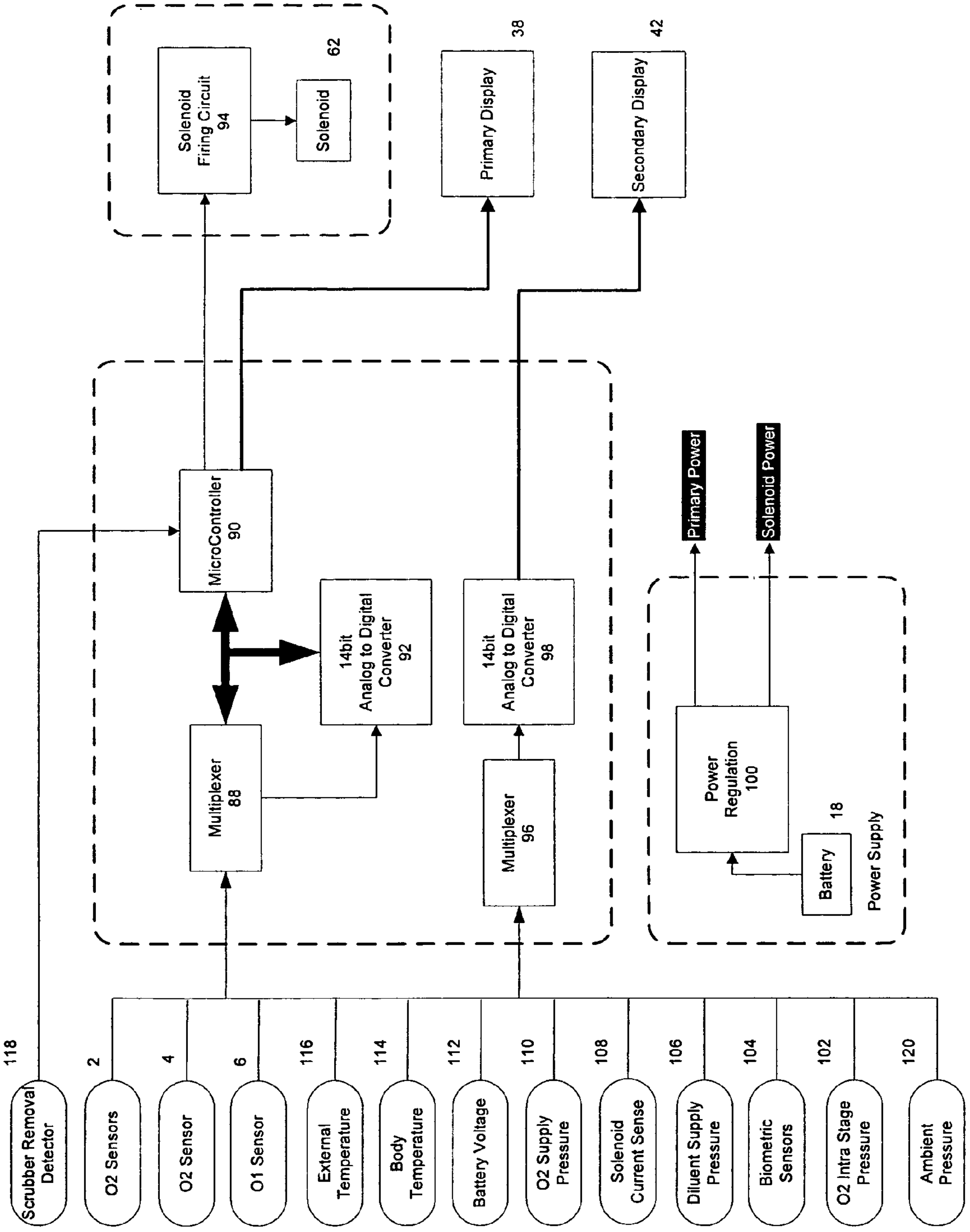
FIG. 6 is a schematic block diagram of the example modular controller.

For purposes of example, this preferred embodiment is demonstrated on a closed circuit breathing system known as an MK15 style electronically controlled mixed gas closed circuit underwater rebreather (FIG. 1) which has had its scrubber housing (FIGS. 3 and 4) and external case modified to accept the modular controller assembly (FIG. 2).

This example describes a mechanical module which serves as a containment for the electronic, mechanical and sensor components of the control system as referenced in claim 1. Other configurations as outlined in the claims are possible and practical such as remote, non-module contained sensors or use in other types of breathing systems.

The modularized control system for this example is a microcontroller based system with the hardware and software necessary to provide the ability to sense the partial pressure of Oxygen within a breathing loop using standard Oxygen partial pressure sensors such as Teledyne R22Ds [available from Oxycheq.com]. (2, 4 and 6). The controller (22) and associated firmware also has the ability to control the injection of low pressure (standard SCUBA interstage pressures of between 165 psi and 95 psi) Oxygen with a solenoid (62) such as the Wattmiser model by SnapTite [2W12w-1NB-V0A4 distributed by FasanAll] into a breathing loop.

The mechanical module (22) is made of Delrin and machined in such a way as to create an o-ring gland (20) on one end to facilitate a bore-seal (28) into the breathing loop area of the rebreather scrubber canister housing (24). The inside of this module is machined such that a printed circuit board may be placed inside in a manner which allows encapsulation by a potting material, such as Epic S7285. Towards the end of the module (22), which is placed into the rebreather scrubber canister housing (24), are gas path and access holes sufficient to provide for the removal and replacement of the gas sensors (2, 4, and 6) as well as providing a vent port (12) connected to the output port of the gas solenoid (62).

There is a low pressure (less than 200 psi), $O_2$ cleaned, gas fitting mounted on the inside of the module (22). The inside of the module (22) at the point of the gas entry (14) is machined such that a gas-tube barb may be fitted on the inside of the module (22) and provide a low pressure gas tube fitting to the input port of the gas solenoid (62).

An isolation barrier is formed by the isolation gasket (8) machined into the controller module (22) to provide separation between the inhalation and exhalation sections of the scrubber housing (24).

A printed circuit board (PCB) is manufactured (using industry standard printed circuit board techniques such as created with ORCAD Capture/Layout and ordered through PCBPRO.com) which is shaped to conform to the area defined inside the module (22). The PCB provides a means for mechanical placement and circuit communications and control paths between the elements of the control subsystem including the gas control solenoid (62) and said Oxygen sensors (2, 4 and 6). The PCB also provides for the means of electrical interconnection to waterproof bulkhead protected cables (10 and 16) which are mounted on the side of the module (22). These cables, (10 and 16), provide a signal interconnect for the user worn primary (38) and secondary (42) display devices.

The top of the module (22) provides a separate waterproof compartment (18) for the installation of a standard alkaline 9 volt battery (18) which provides power to the plurality of control system components.

The control subsystem is defined by several main components; a microprocessor (90) such as the Motorola MC68HC908JL8CDW (FIG. 1-13) [MC68HC908JL8CDW-ND as ordered through Digikey distribution, an acquisition and measurement subsystem consisting of a multiplexer a Maxim 8:1 analog multiplexer such as a MAX4783EUE [as ordered direct from Maxim-IC.com] (88, 96) and a high resolution (34 bit) Analog-to-Digital converter such as a Maxim MAX32555ETL [as ordered direct from Maxim-IC.com] (92 and 98), a power supply consisting of a standard 9v battery (18) and standard voltage regulating circuitry (100) such as a Toko 3.3 volt regulator TK73733SCL [TK73733SCL-ND as ordered through Digikey Distribution], a solenoid control subsystem consisting of a solenoid firing circuit (94) and a solenoid Wattmiser model by SnapTite [2W12w-1NB-V0A4 distributed by FasanAll] (62), and sensors and feedback devices consisting of sensors and associated conditioning electronics for sensors (2, 4, 6, 112). Input channels and associated software is provided as necessary for other implementations of additional functional configurations of the modular control system such as external temperature (116), body temperature (114), $O_2$ supply pressure (110), solenoid current sense (108), diluent supply pressure (106), biometric sensors (104), $O_2$ intra-stage pressure sensors (102), and ambient pressure (120).

The circuit components are connected together using a Printed Circuit Board (PCB) using industry standard printed circuit board techniques such as created with ORCAD Capture/Layout such that the shape conforms as necessary to fit the space provided in the module.

In this example the measurement system for the secondary monitor (96, 98) is powered independently by the secondary display so as to decrease the likelihood of linked failures between the primary and secondary system. The acquisition and measurement of the Oxygen sensors (2, 4 and 6) are performed by the secondary display unit (42) via direct control of the multiplexer (96) and ADC (98) by the microcontroller contained within the secondary display unit (42).

The sensors of the system are connected to the multiplexer (88). The output of the multiplexer (88) is in turn connected to the ADC (92). The digital controls of both the analog multiplexer (88) and the ADC (92) are connected to the microprocessor as is the solenoid firing circuit (94) (solid state relay such as IR PVN012) which fires the gas addition solenoid (62).

The primary control system microprocessor (90) has sufficient inputs and outputs such that the embodied firmware may calculate all appropriate considerations into a sufficiently accurate level of partial pressure of Oxygen within the breathing loop for and during human inhalation and exhalation.

The firmware will then make a determination as to the need for addition of Oxygen by the module (22) into the breathing loop (24). If necessary, the firmware in the microprocessor (90) will utilize the solenoid control subsystem (94) to cause the solenoid (62) to open for a sufficiently long duration such that sufficient Oxygen is added to the breathing system to maintain the desired level of Oxygen within the breathing system.

Additional firmware is embodied such that the user primary display device (38) may inform the user of low battery and other error conditions as well as of the level of Oxygen in the system. The control subsystem is enabled to turn on via action of a pressure switch (110) acting on the systems intermediate Oxygen pressure as detected in the gas flow path (14).

The firmware for accomplishing the above tasks is written in assembly language and downloaded using standard industry programming devices specific for the processor of choice. The firmware is structured in a number of extensible code spaces divided between interrupt driven timed structures and loop driven structures. The time driven structures provide timed standard code spaces with the time intervals occurring at 200 us, 10 ms, 50 ms, 100 ms, 1 sec, 10 sec, 1 minute, and 1 hour. The loop driven structures are divided between a Primary Loop and two Round-Robin Loop spaces. All code spaces in the Primary Loop space are executed through the entire loop space as frequently as possible but without regard to exact time. One of the Round-Robin code spaces is executed once per pass of the Primary Loop code space and is used for less time critical applications.

The overall code structure is divided between 3 levels of functions dealing with Core, Standardized Support, and Application Specific code functions—all code in those spaces executing in one of the above mentioned timed or loop driven code spaces. Each of the measurement functions is carried out on a timed and table driven process which accumulates one set of measurements every 50 ms. As each measurement is selected, the multiplexer is set to pass that measurement parameter through to the ADC (Analog to Digital Converter), the ADC is then instructed to make the measurement which is then stored in RAM in the microprocessor. This is a Round-Robin process initiated by a timer in the 50 ms code space. Execution Flags are set as each measurement is taken to cause an additional Round-Robin process to execute which averages the value of each measurement and determines if the measurement is valid in terms of ADC functionality.

The $PO_2$ evaluation consists of a number of steps. These steps are to first acquire the raw ADC readings. These are then averaged and turned into voltage readings for each sensor. These are stored and also translated via the calibration variables to $PO_2$ values. The $PO_2$ and millivolt values are examined for each sensor for validity and low level error bits are set accordingly for each sensor as required. For the sensors that are determined to have valid readings, they are averaged together and then evaluated individually relative to the averaged value to determine if it is in fact valid to include each sensor in the average. Sensors that are too far apart must have different algorithms applied to determine the most likely true $PO_2$ level. Appropriate High and Low Level errors are set depending both on the relationship of the sensors to each other as well as the resultant $PO_2$ determination.

History Transmission: A generic core based queue management system is used to handle multiple RS232 transmission requests. This system manages the task of transmitting a block of data byte by byte and does not require any other involvement from the applications code except to provide a request flag set and to provide the necessary data pointers to the block of data. Once the transfer is complete, the system sets a data transfer complete flag that is specific to each data request to enable any action that is waiting on that specific transfer.

Watchdog Timer: This is a firmware driven timer that exists to validate the selection and execution of either the Diagnostic Mode or the Active Mode. This is meant to monitor the system for major errors in internal program flow has not engaged one of the two major wakeup modes. If triggered and the unit is the Master, it will declare a high level error and attempt to failover to the lower processor. If the lower processor does not exist, the Active Mode will attempt to be forced.

Low Battery Detection: Both battery inputs have an ADC request generated once per 100 ms. This is averaged in a Round Robin routine and then translated from the resistor divider output level into true battery voltage levels. These levels are then compared against thresholds for error conditions and appropriate flags are set. This is a Low Level error since even if the battery is too low to fire the solenoid, there will be no High Level error generated except as the $PO_2$ reaches a dangerously low level of $0.18PO_2$.

Fault System: The fault system consists of a High and Low level tracking system. Each specific error is generated by individual independently operating routines. These errors are usually in bytes or flags specific to each area of operation. Once per second, these errors are translated into High and Low Level error bytes that are then checked by the Active and Diagnostic Mode routines.

In addition to the core structure, the Generic Core provides a number of processes to support the applications code. These consist of the SPI and RS232 request queue management and drivers for external communications, multiple pushbutton debounce and state management, internal ADC support, and Math routines.

Sensor Data Management: Sensor data management is the core critical process of the controller. This is the process that determines the best truth to be obtained from 3 channels and the connected 3 sensors regarding the level of Oxygen in the monitored breathing loop. At first glance, this is not a complicated process. Most implementations of breathing loop controllers will address determining the "correct" Oxygen level from three good sensors with one of several philosophies—The differences that those philosophies produce in reported $PO_2$ levels are negligible. Due to the malleability of the output of fuel cell based Oxygen sensor cells, it is a standard practice to detect and allow for a sensor to be out of range of the other sensors by averaging the remaining two sensors. The definition of "out of range" is arbitrary and differences in out of range definitions do not produce significantly different $PO_2$ results. These standard approaches produce acceptable results under these limited circumstances of predominately functional sensors and measurement systems.

In addition, it is common to apply the same rules for Oxygen level determination for all purposes such as Solenoid Control, Operator Display, Alarm Control, and Calibration Condition. While applying the same rules for determining Oxygen levels for these purposes makes sense when everything is predominately functional, as conditions degrade for whatever reason, the requirements of each purpose may diverge and one Oxygen Level determination process will no longer produce optimum results. As an example, the situation of all three sensors producing greatly divergent readings results in different demands from the above listed processes: Operator $O_2$ Display has a mandate to display the known $PO_2$ level but in this case, there is no means of determining an actual $PO_2$ level and the most appropriate display is to indicate an error condition. The Solenoid Control process has the primary goal of maintaining a defined setpoint. A secondary goal is to behave in a manner most likely to keep the operator alive regardless of the inexactness of the precise Oxygen level. In this case, since it is more likely that sensors are falsely low due to the chemistry of their construction; the averaging of the two highest sensors is most likely to produce an Oxygen level that may not be accurate but will remain within a livable Oxygen level. The Alarm Control's job is to indicate when it is likely that the Oxygen level has reached a dangerous level. In this case, since it is not known which if any of the sensors are accurate, it is necessary and desirable to err on the conservative side more so than the Solenoid Control system. A meaningful system would be to allow the alarm for $O_2$ dangerously high to be run by the highest sensor alone since that is the most likely to be accurate due to the most common causes of $O_2$ failure. On the other hand, the alarm for $O_2$ dangerously low conditions would run off the average of the two lowest sensors. This is due to the most likely failure mode being to produce a output lower than the actual Oxygen level. The average of the two lowest sensors will produce an Alarm Level that will functionally catch an actual dangerously low $O_2$ level if there is any nominal relationship between the sensor outputs and actual $O_2$ levels, there is a much better chance that these rules under this circumstance will produce far more meaningful results than simply using the same approach for all purposes. These rules change a number of times depending on both what the sensors are outputting relative to one another then also change again when additional error sources are taken into account such as wire breaks, failures in connectors or measurement electronics, etc.

The result of all this is a dual level matrix of rules. The first level associates the 4 main processes (Display, Solenoid, Alarm, and Calibration Condition) to the number of sensors that are producing information that is assessed as meaningful (3 channels, 2 channels, 1 channel, no channels). In each of these 16 rule areas, the output of the existing sensors are also assessed in a matrix determining the explicit rules for all of the circumstances of how close or not the sensors are tracking each other (3 close, 2 close, none close) for each of the 4 main processes listed above.

The exact nature of an expanded rule generation for different purposes may change depending on the philosophies of the designers and/or upon the explicit operational or design goals of the system but the elements of accessing different processes with different rules makes significant contributions to the ability to maintain mission capable system in the event of system failures or functional degradations. As in the example above, it is possible to function with one simple rule for all purposes (such as use the middle sensor), it may not always produce as meaningful a result under all possible circumstances.

We claim:

1. A control subsystem for a breathing device comprising a microcontroller, measurement electronics for receiving sensed signals, at least one connector, at least one gas control solenoid configured to inject gas into a breathing loop of the breathing device, at least one gas connection configured to provide gas communication between the control subsystem and the breathing device, and software configured to monitor gas in the breathing device and control the at least one gas control solenoid, wherein the control subsystem is modular and removably attachable to the breathing device.

2. The control subsystem of claim 1 comprising a low pressure Oxygen measurement subsystem.

3. The control subsystem of claim 1 comprising a mid (intra-stage) pressure measurement subsystem.

4. The control subsystem of claim 1 comprising a high pressure gas measurement subsystem.

5. The control subsystem of claim 1 comprising a system power supply.

6. The control subsystem of claim 1 comprising at least one barometric sensor and a pressure sensing measurement subsystem.

7. The control subsystem of claim 1 comprising at least one wireless transceiver configured to communicate data to and from at least one measurement subsystem.

8. The control subsystem of claim 1 comprising at least one wireless transceiver configured to communicate data between the control subsystem and at least one display/input device.

9. The control subsystem of claim 1 comprising a Personal Alert Safety System (PASS) subsystem.

10. The control subsystem of claim 1 further comprising at least one oxygen sensor configured to sense a partial pressure of oxygen within a breathing loop of the breathing device.

11. The control subsystem of claim 10 wherein the at least one oxygen sensor is situated within a boundary defined by the control subsystem.

12. The control subsystem of claim 10 further adapted to interface with the breathing loop of the breathing device so as to expose the at least one oxygen sensor to a gas in the breathing loop.

13. The control subsystem of claim 10 further comprising a mid (intra-stage) pressure measurement subsystem.

14. The control subsystem of claim 13 further comprising a high pressure gas measurement subsystem.

15. The control subsystem of claim 1 further comprising a diluent supply pressure measurement subsystem.

16. The control subsystem of claim 1 further comprising input and output cabling configured to:

communicate data to and from at least one measurement subsystem; and communicate data between the control subsystem and at least one display/input device.

17. A control subsystem for a breathing device comprising:

a sensor means for sensing gas in a breathing loop;

a microcontroller means for monitoring and maintaining the breathing loop gas;

a data transmission means for receiving and sending input and output signals;

a solenoid means for injecting gas into the breathing loop; and a connection means for accommodating the control subsystem as a modular control subsystem, wherein the modular control subsystem is removably attachable to the breathing device.

* * * * *